United States Patent
Fu et al.

(10) Patent No.: US 11,039,959 B2
(45) Date of Patent: Jun. 22, 2021

(54) OPHTHALMIC LASER SURGICAL SYSTEM AND METHOD FOR CORNEAL LENTICULAR INCISIONS WITH UNAMBIGUOUS ENTRY CUTS

(71) Applicant: AMO Development, LLC, Santa Ana, CA (US)

(72) Inventors: Hong Fu, Pleasanton, CA (US); Alireza Malek Tabrizi, Fremont, CA (US); Nima Khatibzadeh, San Jose, CA (US); James Hill, Santa Ana, CA (US)

(73) Assignee: AMO Development, LLC, Santa Ana, CA (US)

( * ) Notice: Subject to any disclaimer, the term of this patent is extended or adjusted under 35 U.S.C. 154(b) by 277 days.

(21) Appl. No.: 16/121,482

(22) Filed: Sep. 4, 2018

(65) Prior Publication Data
US 2020/0069470 A1    Mar. 5, 2020

(51) Int. Cl.
*A61F 9/008*    (2006.01)

(52) U.S. Cl.
CPC ........ *A61F 9/00827* (2013.01); *A61F 9/0084* (2013.01); *A61F 2009/0087* (2013.01); *A61F 2009/00872* (2013.01); *A61F 2009/00897* (2013.01)

(58) Field of Classification Search
CPC ............... A61F 9/00827; A61F 9/0084; A61F 2009/0087
See application file for complete search history.

(56) References Cited

U.S. PATENT DOCUMENTS

| | | |
|---|---|---|
| 4,764,930 A | 8/1988 | Bille et al. |
| 5,993,438 A | 11/1999 | Juhasz et al. |
| 6,315,413 B1 | 11/2001 | Shimmick et al. |
| 8,260,024 B2 | 9/2012 | Farrer et al. |
| 9,572,716 B2 | 2/2017 | Russmann et al. |
| 2011/0172649 A1 | 7/2011 | Schuele |
| 2013/0281922 A1 | 10/2013 | Seiler et al. |
| 2015/0057644 A1 | 2/2015 | Skerl |
| 2016/0089270 A1* | 3/2016 | Fu ...................... A61F 9/00827 606/5 |
| 2016/0374857 A1 | 12/2016 | Fu et al. |
| 2018/0000647 A1 | 1/2018 | Malek et al. |

FOREIGN PATENT DOCUMENTS

DE    102008049401 A1    4/2010

* cited by examiner

*Primary Examiner* — Joseph M Dietrich
(74) *Attorney, Agent, or Firm* — Johnson & Johnson Surgical Vision, Inc.

(57) ABSTRACT

An ophthalmic laser procedure for forming a lenticule in a cornea and extracting the lenticule from the cornea to accomplish vision correction. An ophthalmic laser system is used to form top and bottom lenticule incisions defining a lenticule in between, and further to form top and/or bottom entry cuts that respectively end unambiguously near the top or bottom lenticule surface. The bottom entry cut intersects both the top and bottom lenticule incisions but ends near the bottom lenticule incision. The entry cuts allow the surgeon to insert a surgical tool which reaches the intended top or bottom lenticule surface without ambiguity. The lenticule has an optical zone in the center that defines the optical power of the lenticule, and a transition zone in the periphery, where the end points of the entry cuts are located in the transition zone.

11 Claims, 6 Drawing Sheets

OPHTHALMIC LASER SURGICAL SYSTEM AND METHOD FOR CORNEAL LENTICULAR INCISIONS WITH UNAMBIGUOUS ENTRY CUTS

BACKGROUND OF THE INVENTION

Field of the Invention

Embodiments of this invention relate generally to laser-assisted ophthalmic procedures, and more particularly, to systems and methods for lenticular incisions in the cornea and lenticule extraction.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SmILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In the SmILE procedure, instead of ablating corneal tissue with an excimer laser following the creation of a corneal flap, the technique involves tissue removal with two femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

Figure 1A:
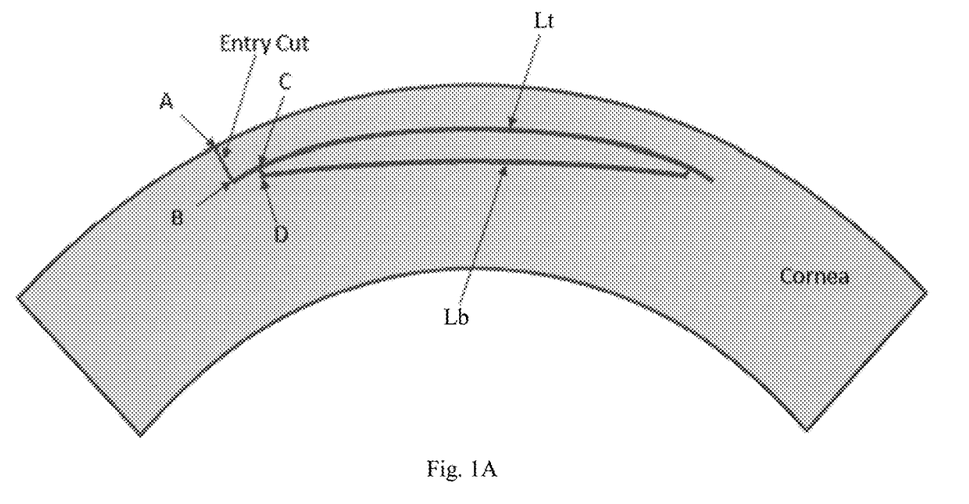
FIGS. 1A and 1B illustrate corneal lenticule incisions in existing corneal lenticule extraction methods.

FIG. 1A schematically illustrates a side cross-sectional view of a lenticule incision in a cornea, the cross-section being cut through a central axis of the cornea. The incisions include a bottom lenticule surface incision Lb, a top lenticule surface incision Lt, an edge cut, and an entry cut. The bottom and top lenticule surface incisions have spherical or other curved shapes and are typically circular or elliptical when viewed from the top. The tissue between the top and bottom surfaces is the lenticule. The entry cut extends from the cornea surface to the top lenticule surface at a location outside of the edge CD of the lenticule. when viewed from the top (not shown), the surface opening A is arc shaped or a straight line in the tangential direction with a relatively small length, such as a few mm. These cuts are formed using a laser beam, such as a femtosecond pulsed laser beam. After forming the incisions, the surgeon inserts a surgical tool, such as a surgical spatula or surgical tweezers, through the entry cut, to separate the lenticule tissue at the top and bottom lenticule surfaces from the remaining cornea tissue. The surgeon then uses the same or another surgical tool to grab and extract the lenticule from the cornea through the entry cut.

Figure 1B:
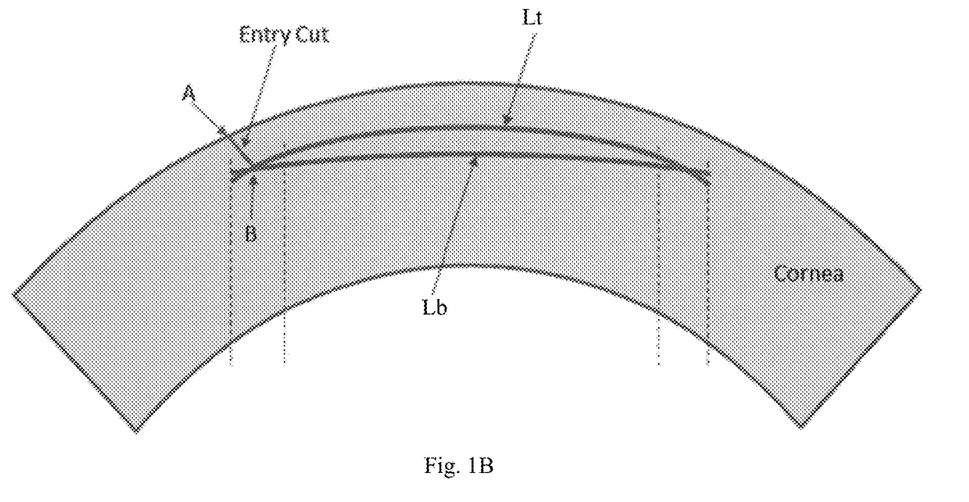

FIG. 1B schematically illustrates a side cross-sectional view of another lenticule incision in a cornea. The incisions include a bottom lenticule surface incision Lb, a top lenticule surface incision Lt, and an entry cut. The top and bottom lenticule surfaces intersect each other at a closed line, e.g., a circle, forming the edge of the lenticule, and extend beyond the edge of the lenticule. The entry cut AB reaches from the surface point A to the point B on the intersection line of the top and bottom lenticule surfaces. The separation and extraction steps are similar to those in the example shown in FIG. 1A.

SUMMARY OF THE INVENTION

To obviate one or more problems due to limitations and disadvantages of the related art, embodiments of the present invention provide a method for extracting a lenticule from a cornea of a patient's eye, which includes: operating an ophthalmic surgical laser system to form a top lenticule surface incision and a bottom lenticule surface incision in the cornea, the top and bottom lenticule surface incisions intersecting each other at a closed line defining a lenticule edge, the top and bottom lenticule incisions forming a lenticule of corneal tissue between them; and operating the ophthalmic surgical laser system to form a top entry cut in the cornea, the top entry cut having a shape that starts from a top surface of the cornea, extends downwardly and inwardly, intersects the top lenticule surface incision at an intersection location, and ends at an end location inside the lenticule, wherein the end location is at a distance between 3 to 40 microns from the intersection location, and wherein at the intersection location, an angle between a portion of the top entry cut above the intersection location and a portion of the top lenticule surface incision inside of the intersection location is an acute angle.

In another aspect, the present invention provides a method for extracting a lenticule from a cornea of a patient's eye, which includes: operating an ophthalmic surgical laser system to form a top lenticule surface incision and a bottom lenticule surface incision in the cornea, the top and bottom lenticule surface incisions intersecting each other at a closed line defining a lenticule edge, the top and bottom lenticule incisions forming a lenticule of corneal tissue between them; and operating the ophthalmic surgical laser system to form a bottom entry cut in the cornea, the bottom entry cut having a shape that starts from a top surface of the cornea, extends downwardly and inwardly, intersects the top lenticule surface incision at a first intersection location, extends within the lenticule, intersects the bottom lenticule surface incision at a second intersection location, and exits the lenticule and ends at an end location outside the lenticule, the end locating being at a distance between 3 to 40 microns from the second intersection location.

In another aspect, the present invention provides an ophthalmic surgical laser system, which includes: a laser system configured to generate a pulsed laser beam; an optical delivery system configured to deliver the published laser beam to a cornea of a patient's eye, including a scanner system configured to scan a focus spot location of the pulsed laser beam within the cornea; a controller configured to control the laser system and the scanner system to: scan the focus spot location of the pulsed laser beam within the cornea to form a top lenticule surface incision in the cornea; scan the focus spot location of the pulsed laser beam within the cornea to form a bottom lenticule surface incision in the cornea, wherein the top and bottom lenticule surface incisions intersect each other at a closed line defining a lenticule edge, the top and bottom lenticule incisions forming a lenticule of corneal tissue between them; scan the focus spot location of the pulsed laser beam within the cornea to form a top entry cut in the cornea, the top entry cut having a shape that starts from a top surface of the cornea, extends downwardly and inwardly, intersects the top lenticule surface incision at a first intersection location, and ends at first end location inside the lenticule, wherein the first end location is at a distance between 3 to 40 microns from the first intersection location, and wherein at the first intersection location, an angle between a portion of the top entry cut above the first intersection location and a portion of the top lenticule surface incision inside of the first intersection location is an acute angle; and scan the focus spot location of the pulsed laser beam within the cornea to form a bottom entry cut in the cornea, the bottom entry cut having a shape that starts from the top surface of the cornea, extends downwardly and inwardly, intersects the top lenticule surface incision at a second intersection location, extends within the lenticule, intersects the bottom lenticule surface incision at a third intersection location, and exits the lenticule and ends at a second end location outside the lenticule, wherein the second end location is at a distance between 3 to 40 microns from the third intersection location.

In one embodiment, a central portion of the top lenticule surface incision is a part of a sphere, and a peripheral portion of the top lenticule surface incision outside of the central portion has a steeper shape than the sphere, and wherein the intersection location of the top entry cut and the top lenticule surface incision is located in the peripheral portion of the top lenticule surface incision or at a boundary between the central portion and the peripheral portion of the top lenticule surface incision.

In one embodiment, a central portion of the bottom lenticule surface incision is a part of a sphere, and a peripheral portion of the bottom lenticule surface incision outside of the central portion has a steeper shape than the sphere, and wherein the intersection location of the bottom entry cut and the bottom lenticule surface incision is located in the peripheral portion of the bottom lenticule surface incision or at a boundary between the central portion and the peripheral portion of the top lenticule surface incision.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF PREFERRED EMBODIMENTS

Embodiments of this invention are generally directed to systems and methods for laser-assisted ophthalmic procedures, and more particularly, to systems and methods for corneal lenticule incision and extraction.

A problem with the lenticule incision and the extraction procedure described earlier is that, when the surgical tool is inserted through the entry cut to the edge of the lenticule, the surgeon cannot easily control and judge whether the tip of the tool is reaching at the top lenticule surface or at the bottom lenticule surface. In the example shown in FIG. 1A, when the surgeon inserts the surgical tool through the entry cut from the surface point A to the end point B where the entry cut intersects the top lenticule surface, and further moves the tip inwardly to point C at the lenticule edge CD, the surgeon cannot easily control and judge whether the tip of the tool will reach the top or the bottom lenticule surface. In other words, when the tip is moved further inward from point C, it may move along either the top lenticule surface or the bottom lenticule surface. This is partly because the tip of the tool is normally thicker than the lenticule edge thickness CD (typically less than 15 μm). Similarly, in the example shown in FIG. 1B, when the tip of the tool is inserted through the entry cut AB and reaches the point B, where the top and the bottom lenticule surfaces intersect, there is no guidance for the tip of the tool to further move along a specific (top or bottom) lenticule surface. Thus, the surgeon cannot easily control and judge whether the tip of the tool is reaching the top or the bottom lenticule surface.

Usually, in order to minimize tissue distortion during extraction, surgeons prefer to perform separation on the top lenticule incision first, because it involves stronger corneal tissue than the bottom one and therefore more chances to have residual tissue bridges after laser incision, and because the tissue layer above the top surface is thinner and therefore needs to be handled with fewer possibly moving tissue parts. Therefore, the inability to control which surface the tip of the tool reaches presents a problem for the surgeon. The surgeon needs to try to determine which surface the tool is at, and may need to re-insert the tool to reach the intended surface. This is an undesirable step in the surgery process. Further, such steps also introduce a risk by migration of the epithelial cells from the surgical tool. The motion, pushing across and swiping side to side, to free the tissues from the stroma can possibly deposit epithelial cells into the stroma tissues, especially when the tool is not completely rinsed by the surgeon during the procedure, creating a condition such as epithelial in-growth.

Embodiments of the present invention provides a method for creating lenticule entry cut that leads the surgical tool to a specified (the top or the bottom) lenticule surface in a definitive manner.

Figure 2:
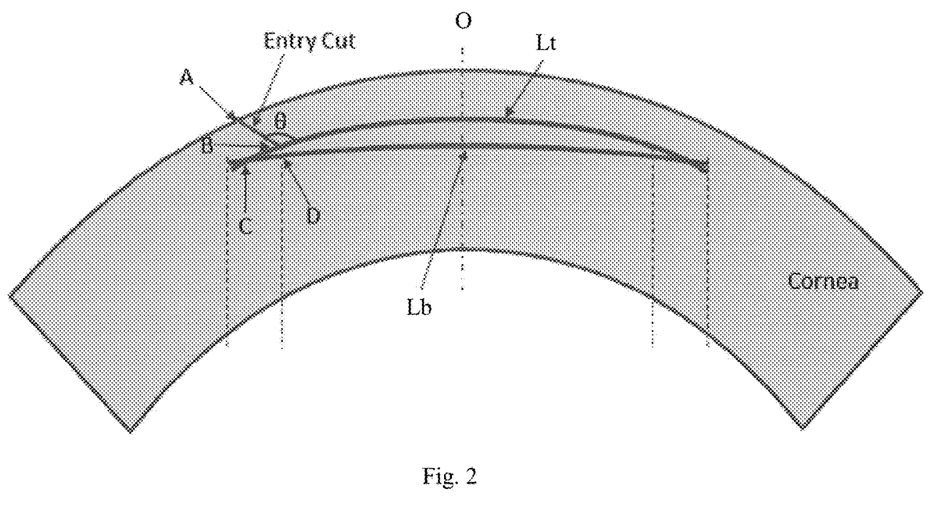
FIG. 2 illustrates corneal lenticule incisions in a corneal lenticule extraction method according to an embodiment of the present invention.

FIG. 2 schematically illustrates a side cross-sectional view of a corneal lenticule incision according to an embodiment of the present invention, where the entry cut is designed to unambiguously reach only the top lenticule surface. The cross-section is cut through a central axis O of the cornea. As shown in FIG. 2, the lenticule incisions of this embodiment includes a top lenticule surface incision Lt, a bottom lenticule surface incision Lb, and an entry cut AB. The bottom and top lenticule surface incisions have spherical or other curved shapes, and may be circular or elliptical or have other shapes when viewed from the top. The top and bottom lenticule surfaces intersect each other at a closed line C, e.g. a circle, forming the edge of the lenticule, and extend beyond (outside of) that edge. The tissue between the top and bottom surfaces is the lenticule. The entry cut AB extends from a location A on the cornea surface to the top lenticule surface at a location B inside of the lenticule edge C (the intersection line of the top and bottom lenticule surfaces); i.e., the end point B of the entry cut is closer to the central axis O of the lenticule than the edge C is. When viewed from the top (not shown), the surface opening A and the end point B of the entry cut are arc shaped or straight lines in the tangential direction, with a length of a few mm.

In the side cross-sectional view shown in FIG. 2, the entry cut AB may be straight or curved, and extends downwardly and inwardly, i.e., the end point B is closer to the central axis O than the surface location A is. At the end point B where the entry cut intersects the top lenticule surface, the angle between the tangential of the entry cut and the normal direction of the top lenticule surface is preferably between 0 and 60 degrees, and more preferably, between 0 and 45 degrees. To put it another way, in FIG. 2, the angle θ between the tangential of the entry cut and the tangential of the top lenticule surface is preferably between 90 and 150 degrees, and more preferably, between 90 and 135 degrees. Thus, when the surgical tool is inserted through the entry cut and the tip of the tool reaches the top lenticule surface at point B, the tip will be guided to move along the top lenticule surface (and only along the top lenticule surface) toward the center of the top lenticule surface. This eliminates the unambiguity as to which lenticule surface the tool is on.

This range of the angle between the entry cut and the top lenticule surface described above is optimized for easy movement of the tip along the top lenticule surface while taking other factors into consideration. Importantly, it avoids forming too small an acute angle between the entry cut and the peripheral portion of the top lenticule surface located outside of the entry cut, or between the entry cut and the surface of the cornea, where such acute angles may form thin pieces of cornea tissue which may be prone to tearing or other damage.

Figure 3A:
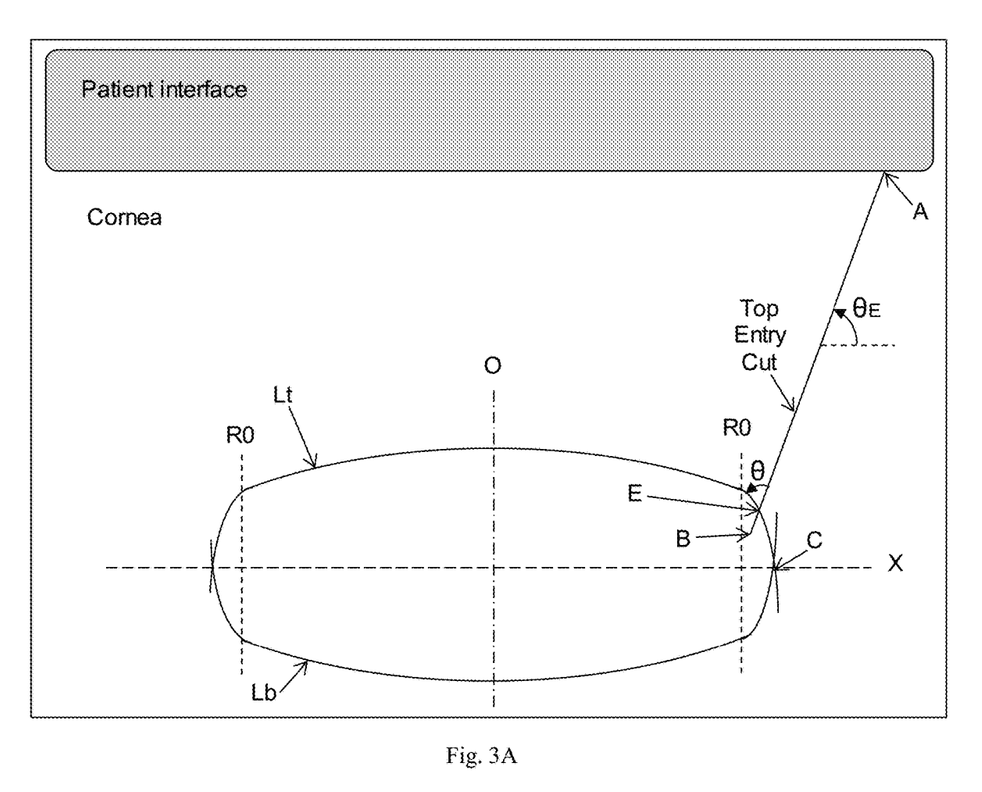
FIGS. 3A and 3B illustrate corneal lenticule incisions in corneal lenticule extraction methods according to other embodiments of the present invention.

FIG. 3A schematically illustrates a side cross-sectional view of a corneal lenticule incision according to another embodiment of the present invention, where a top entry cut is designed to unambiguously reach only the top lenticule surface incision. In this embodiment, a patient interface device is coupled with the patient's eye, such that the cornea is in contact with a surface of the patient interface and conforms to the shape of the contact surface (which may be planar or curved). The other end of the patient interface is coupled to the laser system, and the treatment laser beam is delivered to the eye through the patient interface. After the lenticule incisions and the entry cut are formed, the eye is released from the patient interface, and the lenticule is extracted via the entry cut.

The top and bottom lenticule surface incisions Lt and Lb are formed first. The top and bottom lenticule surfaces incisions intersect each other at a closed line C, forming the edge of the lenticule, and extend beyond the edge. In the illustrated embodiment, the top and bottom lenticule surfaces Lt and Lb are mirror symmetrical to each other with respect to a horizontal center plane (one of the horizontal axis X is shown in the figure); in other embodiments, they may not be mirror symmetrical. The top and bottom lenticule surfaces may have circular or elliptical or other shapes in the top view (not shown).

In this embodiment, in the side cross-sectional view, the entry cut starts at the top corneal surface at point A, extends downwardly and inwardly, intersects the top lenticule surface Lt at a point E inside of the edge C, and continues into the lenticule to end at a point B inside the lenticule. The section EB between the intersection point and the end point is an overcut which ensures that the entry cut will intersect the top lenticule surface. The amount of the overcut EB is, for example, a few microns to a few tens of microns (e.g., 3 to 40 microns), but other values may be used. When viewed from the top (not shown), the surface opening A and the end point B of the entry cut are arc shaped or straight lines in the tangential direction, with a length of a few mm (e.g. 1 to 6 mm).

In this embodiment, a central portion of the lenticule within a radius R0 is referred to as the optical zone, as the shapes of the top and the bottom lenticule surfaces within this zone are specifically designed such that the optical zone corresponds to a defined optical power for purpose of vision correction. The peripheral portion outside of the optical zone, located between radius R0 and the edge C of the lenticule (where the top and bottom lenticule surfaces intersect), is referred to as the transition zone, as the shapes of the top and the bottom lenticule surfaces within this zone are designed not based on consideration of the optical power of the zone, but for the purpose of ensuring that the edge of the lenticule does not become too thin and thus prone to tearing during extraction. Thus, for example, while the optical zone of each of the top and bottom lenticule surfaces is a part of a sphere, the corresponding transition zone is not located on the same sphere of the optical zone but rather, have a steeper shape (i.e. more vertically oriented) in the side cross-sectional view than the spherical shape. As a result, a thicker and more rounded edge of the lenticule is formed. This is beneficial for preventing tear at the edge during extraction and for assuring tissue continuity after the lenticule is extracted from the cornea.

The intersection point E of the entry cut is preferably within the transition zone or at the boundary between the optical zone and the transition zone. At the intersection point E, the thickness of the lenticule tissue, defined as the distance between the top and bottom lenticule surfaces in the direction parallel to the central axis O, is sufficiently thick, for example greater than 10 µm, so that the tip of the tool will land on the intended lenticule surface and will not penetrate through the tissue to the bottom lenticule surface.

In the side cross-sectional view, the entry cut is a straight line or near straight line, and the angle $\theta_E$ between the entry cut and the horizontal axis X is preferably between 30 and 90 degrees. Because of the steep shape of the transition zone, at the intersection point E, the angle $\theta$ between the section of the entry cut above the intersection point and the section of the top lenticule surface inside of the intersection point is an acute angle.

The intersection point E may also be located within the optical zone. In such a case, the optical zone should be larger than the visual field of the eye defined by the pupil, so that the entry cut can be located outside of the visual field and does not affect the patient's vision.

Figure 3B:
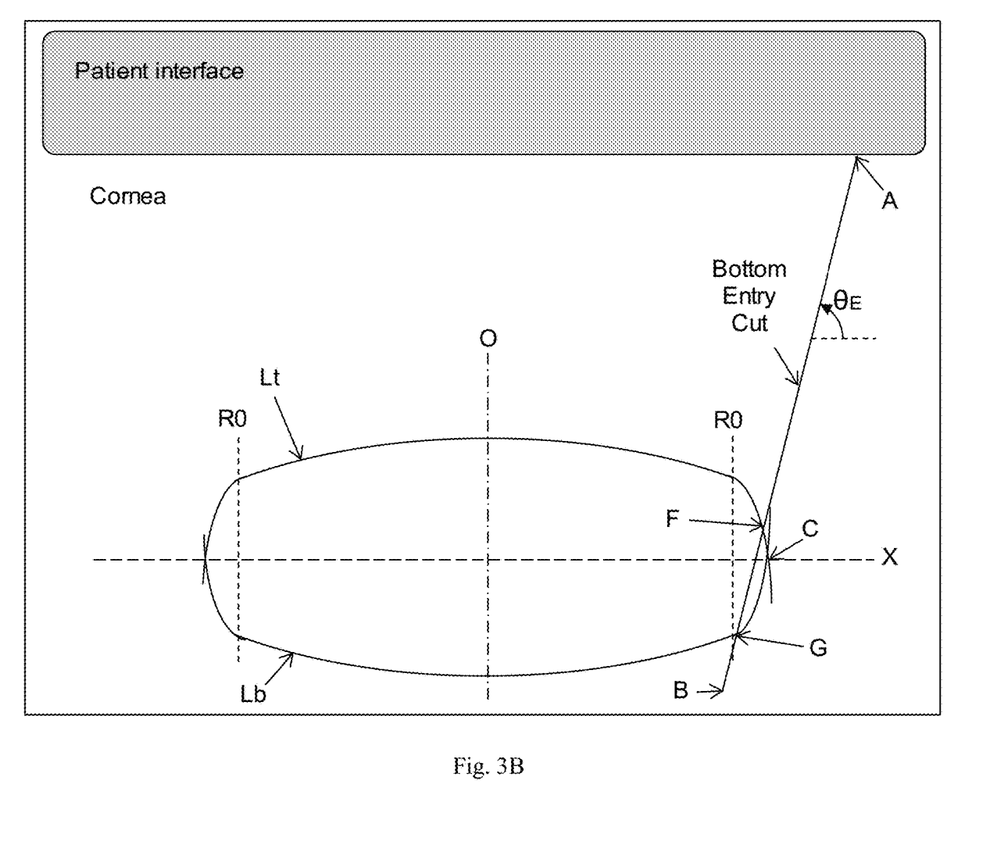

FIG. 3B schematically illustrates a side cross-sectional view of a corneal lenticule incision according to another embodiment of the present invention, where a bottom entry cut is designed to end unambiguously near only the bottom lenticule surface. In this embodiment, the top and bottom lenticule surfaces Lt and Lb are similar or identical to those in the embodiment of FIG. 3A. In this embodiment, in the side cross-sectional view, the bottom entry cut starts at the top corneal surface at point A, extends downwardly and inwardly, intersects the top lenticule surface Lt at a point F inside the edge C, continues into the lenticule and extends towards the bottom lenticule surface, intersects the bottom lenticule surface Lb at a point G inside the edge C, and exits the lenticule to end at a point B outside the lenticule. The section GB between the intersection point G and the end point B is an overcut which ensures that the entry cut will intersect the bottom lenticule surface. The amount of the overcut GB is, for example, from a few microns to a few tens of microns (e.g., 3 to 40 microns), but other values may be used. The intersection point G with the bottom lenticule surface is preferably within the transition zone of the lenticule or at the boundary between the optical zone and the transition zone.

In this embodiment, even though the entry cut intersects the bottom lenticule surface as well as the top lenticule surface, the end point B is located much closer to the bottom lenticule surface than to the top lenticule surface; therefore, when the surgical tool reaches the end point B, it is near the bottom lenticule surface, and there will be no unambiguity as to whether the tool's tip is at the top lenticule surface or the bottom lenticule surface. Thus, the surgeon can manipulate the surgical tool inserted into the bottom entry cut so that the tip of the tool passes the intersection point F with the top lenticule surface and reaches the end point B near the bottom lenticule surface.

In practice, during lenticule extraction procedures, sometimes only one top entry cut and no bottom entry cut is formed, sometimes only one bottom entry cut and no top entry cut is formed, and sometimes two entry cuts are formed and are located at opposite angular locations around the optical axis O in the top view (not shown). The two entry cuts may be a top entry cut and a bottom entry cut, or two top entry cuts, or two bottom entry cuts. The lenticule may be extracted from the top entry cut or the bottom entry cut, and when two entry cuts are formed, the lenticule may be extracted from one of them while the other may be used to assist in the extraction. During the procedure, the surgeon can choose whether to form one or two entry cuts and the type(s) or entry cut(s). Such a choice may be based on individual preference of the surgeon, or factors related to the size and shape of the lenticule to be extracted, or other conditions of the patient's eye.

In the embodiment shown in FIG. 2, the top lenticule surface is convex and the bottom lenticule surface is concave from the perspective of the lenticule; in the embodiments of FIGS. 3A and 3B, both top and bottom lenticule surfaces are convex while the cornea is flattened by the patient interface device. The invention is not limited to any specific shapes of the top and bottom lenticule surfaces. As mentioned earlier, the shapes of the top and bottom lenticule surfaces, at least in the optical zone, are designed based on the optical power correction to be achieved by the lenticule extraction.

In the embodiments described above, the various incisions in the cornea may be performed using any suitable ophthalmic laser system. Described generally, such a laser surgical system includes a laser source for generating a pulse laser beam, an optical system for delivering the laser beam to a target tissue in the eye to form a focus spot therein, the optical system including a scanner system to scan the laser focus spot position in three dimensions, and a controller connected to above components to control and operate them. The laser surgical system preferably also includes measurement and imaging systems to measure and image the structure of the eye. The control system may include a processor executing computer-readable program code stored in a memory, where the program code causes the processor to control the scanner system to scan the laser focus spot according to pre-programed scan patterns to form the various incisions described above.

A laser system that may be used to form the various incisions in embodiments of the present invention is described in more detail below with reference to FIGS. 4 and 5.

Figure 4:
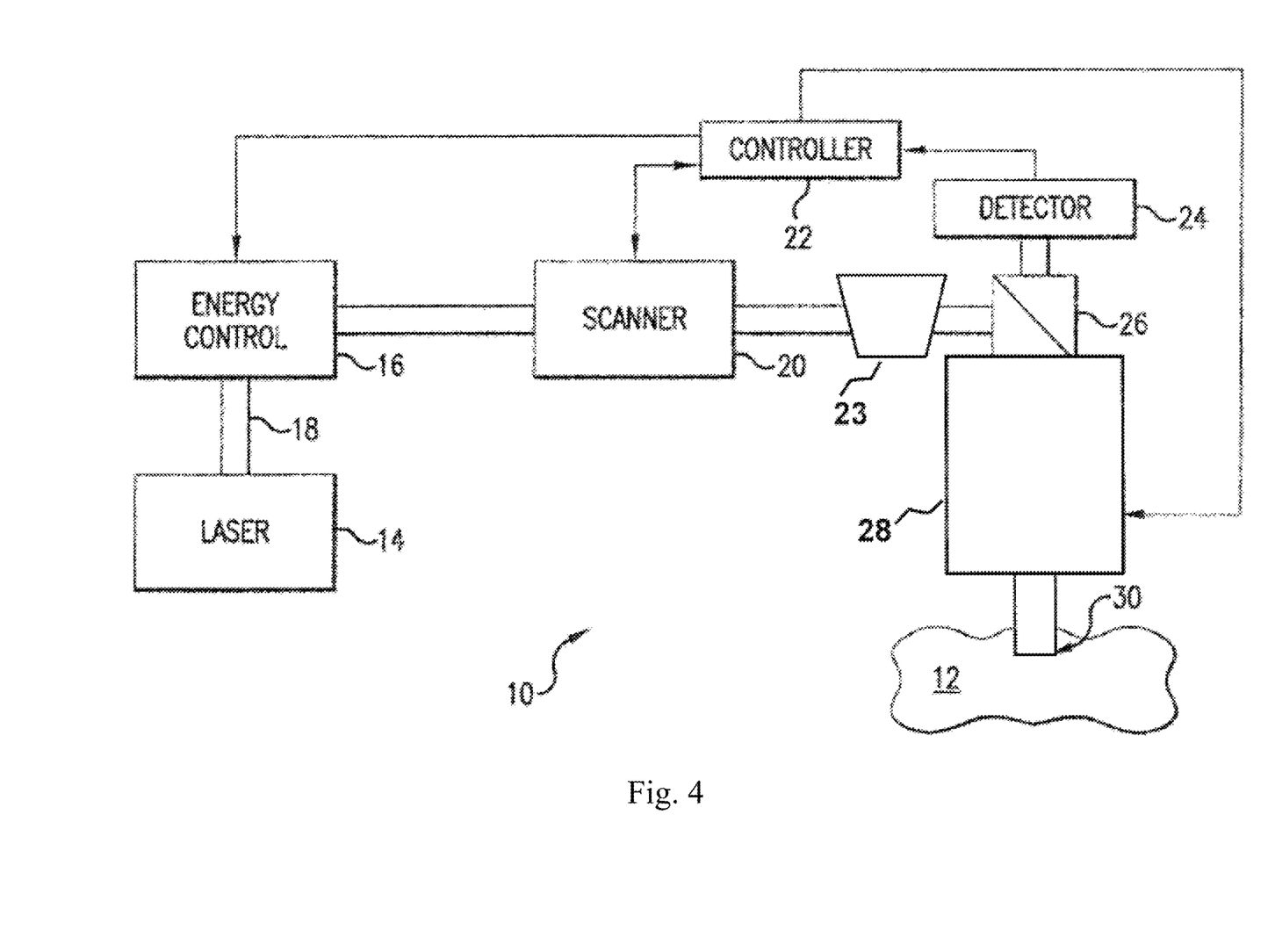
FIG. 4 is a simplified diagram of a surgical ophthalmic laser system that may be used to perform the corneal lenticule extraction methods according to embodiments of the present invention.

FIG. 4 shows a system 10 for making an incision in a material 12 such as the cornea. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor executing suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 5:
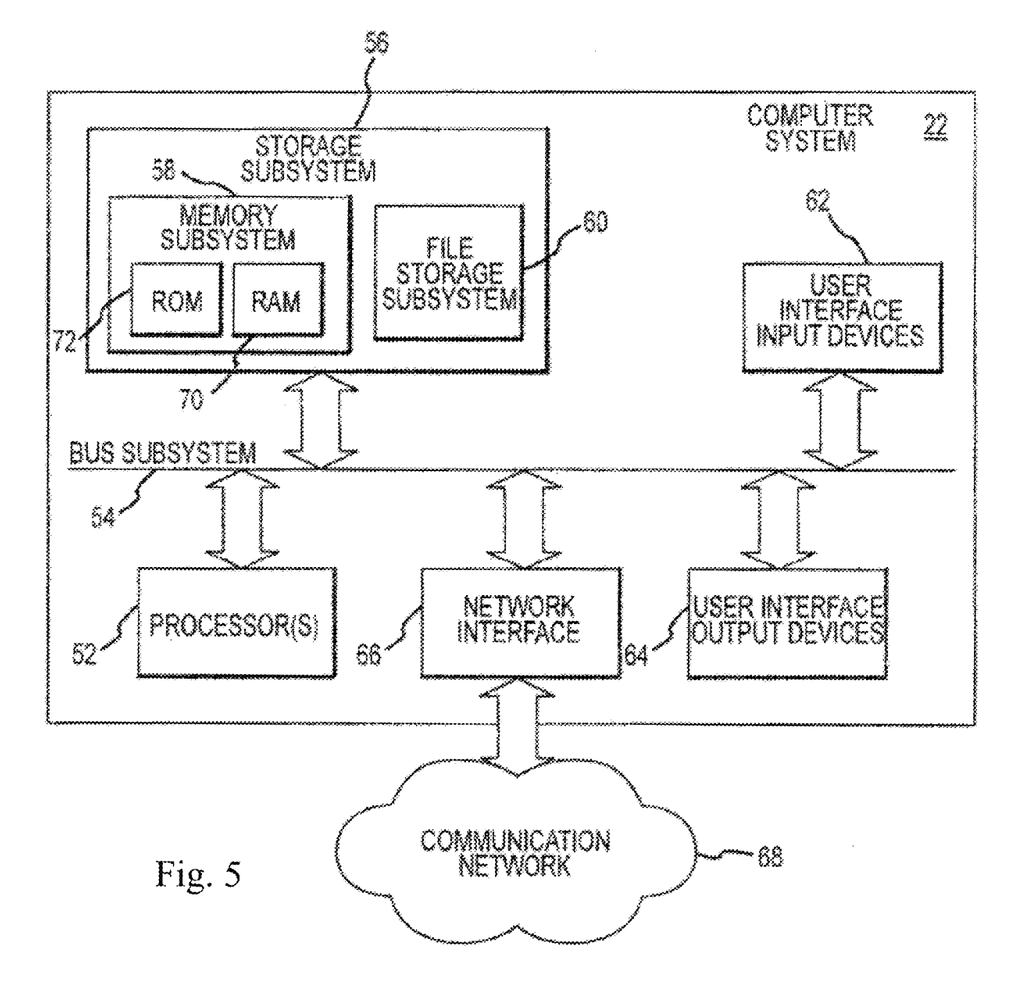
FIG. 5 is a simplified diagram of a controller of a surgical ophthalmic laser system that may be used to perform the corneal lenticule extraction methods according to an embodiment of the present invention.

FIG. 5 illustrates a simplified block diagram of an exemplary controller 22 that may be used by the laser system 10 according to an embodiment of this invention. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 5 is intended only as an example for purposes of illustrating only one embodiment of the present invention. Many other configurations of controller 22, having more or fewer components than those depicted in FIG. 5, are possible.

As should be understood by those of skill in the art, additional components and subsystems may be included with laser system 10. For example, an imaging device or system may be used to guide the laser beam.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

In other embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner); second, the fast scan line is slowly swept by much slower X, Y, and Z scan mechanisms.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method for extracting a lenticule from a cornea of a patient's eye, comprising:
   operating an ophthalmic surgical laser system to form a top lenticule surface incision and a bottom lenticule surface incision in the cornea, the top and bottom lenticule surface incisions intersecting each other at a closed line defining a lenticule edge, the top and bottom lenticule incisions forming a lenticule of corneal tissue between them; and
   operating the ophthalmic surgical laser system to form a top entry cut in the cornea, the top entry cut having a shape that starts from a top surface of the cornea, extends downwardly and inwardly, intersects the top lenticule surface incision at an intersection location, and ends at an end location inside the lenticule, wherein the end location is at a distance between 3 to 40 microns from the intersection location, and wherein at the intersection location, an angle between a portion of the top entry cut above the intersection location and a portion of the top lenticule surface incision inside of the intersection location is an acute angle.

2. The method of claim 1, further comprising, before forming the top and bottom lenticule surface incisions and the top entry cut, coupling the eye to a patient interface device, wherein the cornea contacts a surface of the patient interface device and conforms to a shape of the surface.

3. The method of claim 2, wherein a central portion of the top lenticule surface incision is a part of a sphere, and a peripheral portion of the top lenticule surface incision outside of the central portion has a steeper shape than the sphere, and wherein the intersection location of the top entry cut and the top lenticule surface incision is located in the peripheral portion of the top lenticule surface incision or at a boundary between the central portion and the peripheral portion of the top lenticule surface incision.

4. The method of claim 1, further comprising:
   operating the ophthalmic surgical laser system to form a bottom entry cut in the cornea, the bottom entry cut having a shape that starts from the top surface of the cornea, extends downwardly and inwardly, intersects the top lenticule surface incision at a first intersection location, extends within the lenticule, intersects the bottom lenticule surface incision at a second intersection location, and exits the lenticule and ends at an end location outside the lenticule, the end location of the bottom entry cut being at a distance between 3 to 40 microns from the second intersection location,
   wherein the bottom entry cut and the top entry cut are located at different angular locations around an optical axis of the eye.

5. The method of claim 4, further comprising, before forming the top and bottom lenticule surface incisions and the top entry cut, coupling the eye to a patient interface device, wherein the cornea contacts a surface of the patient interface device and conforms to a shape of the surface;
   wherein a central portion of the top lenticule surface incision is a part of a sphere, and a peripheral portion of the top lenticule surface incision outside of the central portion has a steeper shape than the sphere, and wherein the intersection location of the top entry cut and the top lenticule surface incision is located in the peripheral portion of the top lenticule surface incision or at a boundary between the central portion and the peripheral portion of the top lenticule surface incision, and wherein a central portion of the bottom lenticule surface incision is a part of another sphere, and a peripheral portion of the bottom lenticule surface incision outside of the central portion has a steeper shape than the other sphere, and wherein the intersection location of the bottom entry cut and the bottom lenticule surface incision is located in the peripheral portion of the bottom lenticule surface incision or at a boundary between the central portion and the peripheral portion of the bottom lenticule surface incision.

6. A method for extracting a lenticule from a cornea of a patient's eye, comprising:

operating an ophthalmic surgical laser system to form a top lenticule surface incision and a bottom lenticule surface incision in the cornea, the top and bottom lenticule surface incisions intersecting each other at a closed line defining a lenticule edge, the top and bottom lenticule incisions forming a lenticule of corneal tissue between them; and operating the ophthalmic surgical laser system to form a bottom entry cut in the cornea, the bottom entry cut having a shape that starts from a top surface of the cornea, extends downwardly and inwardly, intersects the top lenticule surface incision at a first intersection location, extends within the lenticule, intersects the bottom lenticule surface incision at a second intersection location, and exits the lenticule and ends at an end location outside the lenticule, the end location being at a distance between 3 to 40 microns from the second intersection location.

7. The method of claim 6, further comprising, before forming the top and bottom lenticule surface incisions and the bottom entry cut, coupling the eye to a patient interface device, wherein the cornea contacts a surface of the patient interface device and conforms to a shape of the surface.

8. The method of claim 7, wherein a central portion of the bottom lenticule surface incision is a part of a sphere, and a peripheral portion of the bottom lenticule surface incision outside of the central portion has a steeper shape than the sphere, and wherein the intersection location of the bottom entry cut and the bottom lenticule surface incision is located in the peripheral portion of the bottom lenticule surface incision or at a boundary between the central portion and the peripheral portion of the top lenticule surface incision.

9. An ophthalmic surgical laser system comprising:

a laser system configured to generate a pulsed laser beam;

an optical delivery system configured to deliver the pulsed laser beam to a cornea of a patient's eye, including a scanner system configured to scan a focus spot location of the pulsed laser beam within the cornea;

a controller configured to control the laser system and the scanner system to:

scan the focus spot location of the pulsed laser beam within the cornea to form a top lenticule surface incision in the cornea;

scan the focus spot location of the pulsed laser beam within the cornea to form a bottom lenticule surface incision in the cornea, wherein the top and bottom lenticule surface incisions intersect each other at a closed line defining a lenticule edge, the top and bottom lenticule incisions forming a lenticule of corneal tissue between them;

scan the focus spot location of the pulsed laser beam within the cornea to form a top entry cut in the cornea, the top entry cut having a shape that starts from a top surface of the cornea, extends downwardly and inwardly, intersects the top lenticule surface incision at a first intersection location, and ends at first end location inside the lenticule, wherein the first end location is at a distance between 3 to 40 microns from the first intersection location, and wherein at the first intersection location, an angle between a portion of the top entry cut above the first intersection location and a portion of the top lenticule surface incision inside of the first intersection location is an acute angle; and scan the focus spot location of the pulsed laser beam within the cornea to form a bottom entry cut in the cornea, the bottom entry cut having a shape that starts from the top surface of the cornea, extends downwardly and inwardly, intersects the top lenticule surface incision at a second intersection location, extends within the lenticule, intersects the bottom lenticule surface incision at a third intersection location, and exits the lenticule and ends at a second end location outside the lenticule, wherein the second end location is at a distance between 3 to 40 microns from the third intersection location.

10. The ophthalmic surgical laser system of claim 9, wherein the bottom entry cut and the top entry cut are located at different angular locations around an optical axis of the eye.

11. The ophthalmic surgical laser system of claim 9, wherein a central portion of the top lenticule surface incision is a part of a sphere, and a peripheral portion of the top lenticule surface incision outside of the central portion has a steeper shape than the sphere, and wherein the first intersection location of the top entry cut and the top lenticule surface incision is located in the peripheral portion of the top lenticule surface incision or at a boundary between the central portion and the peripheral portion of the top lenticule surface incision, and wherein a central portion of the bottom lenticule surface incision is a part of another sphere, and a peripheral portion of the bottom lenticule surface incision outside of the central portion has a steeper shape than the other sphere, and wherein the third intersection location of the bottom entry cut and the bottom lenticule surface incision is located in the peripheral portion of the bottom lenticule surface incision or at a boundary between the central portion and the peripheral portion of the bottom lenticule surface incision.

* * * * *